United States Patent [19]

Na et al.

[11] Patent Number: 5,298,262

[45] Date of Patent: Mar. 29, 1994

[54] USE OF IONIC CLOUD POINT MODIFIERS TO PREVENT PARTICLE AGGREGATION DURING STERILIZATION

[75] Inventors: George C. Na, Fort Washington; Natarajan Rajagopalan, Phoenixville, both of Pa.

[73] Assignee: Sterling Winthrop Inc., New York, N.Y.

[21] Appl. No.: 987,904

[22] Filed: Dec. 4, 1992

[51] Int. Cl.$^5$ .............................................. A61K 9/14
[52] U.S. Cl. .................................... 424/489; 424/499; 424/495; 424/487
[58] Field of Search ............... 424/489, 499, 495, 487; 514/78

[56] References Cited

U.S. PATENT DOCUMENTS

| | | | |
|---|---|---|---|
| 3,272,700 | 9/1966 | Sluppe | 514/535 |
| 4,107,288 | 8/1978 | Oppenheim et al. | 424/499 |
| 4,540,602 | 9/1985 | Motoyama et al. | 424/495 |
| 4,826,689 | 5/1989 | Violanto et al. | 424/489 |
| 4,826,821 | 5/1989 | Clements | 514/78 |
| 5,055,288 | 10/1991 | Lewis et al. | 424/9 |
| 5,133,908 | 7/1992 | Stainmesse et al. | 424/487 |
| 5,145,684 | 9/1992 | Liversidge et al. | 424/489 |

OTHER PUBLICATIONS

"Hydrophile-Lipophile Balance and Cloud Points of Nonionic Surfactants"; J. Pharm Sci., vol. 58, No. 12, Dec. 1969, pp. 1443-1449.

*Primary Examiner*—Thurman K. Page
*Assistant Examiner*—William E. Benston, Jr.
*Attorney, Agent, or Firm*—William J. Davis

[57] ABSTRACT

This invention discloses a composition comprised of nanoparticles having a surface modifier adsorbed on the surface thereof and an anionic or cationic surfactant as a cloud point modifier associated therewith, which cloud point modifier is present in an amount sufficient to increase the cloud point of the surface modifier. A preferred surface modifier is tyloxapol. Preferred anionic surfactants are dioctylsulfonesuccinate, sodium dodecyl sulfate and sodium oleate. Preferred cationic surfactants are dodecyltrimethylammonium bromide and cetrimide tetradecyl ammonium bromide. This invention further discloses a method of making nanoparticles having a surface modifier adsorbed on the surface and an anionic or cationic surfactant as a cloud point modifier associated therewith, comprised of contacting said nanoparticles with the cloud point modifier for a time and under conditions sufficient to increase the cloud point of the surface modifier.

15 Claims, No Drawings

USE OF IONIC CLOUD POINT MODIFIERS TO PREVENT PARTICLE AGGREGATION DURING STERILIZATION

FIELD OF THE INVENTION

This invention relates to therapeutic and diagnostic compositions with a modified cloud point, and to a method for the preparation thereof.

BACKGROUND OF THE INVENTION

Nanoparticles, described in U.S. Pat. No. 5,145,684, are particles consisting of a poorly soluble therapeutic or diagnostic agent onto which are adsorbed a non-crosslinked surface modifier, and which have an average particle size of less than about 400 nanometers (nm).

As a result of their small size, sterilization of therapeutic and diagnostic agents in nanoparticulate form stabilized by a surface modifier (surfactant) is difficult. Filtration using a filter of 0.22 μm mesh size is sufficient to remove most bacteria and viruses, but the nanoparticles, due to their sizes, cannot be sterile filtered. Conventional autoclaving (steam heat) at 121° C. will result in substantial aggregation and/or growth of particle size, rendering the resulting particles unusable.

The aggregation of nanoparticles upon heating is directly related to the precipitation of the surface modifier (surfactant) at temperatures above the cloud point of the surfactant where the bound surfactant molecules are likely to dissociate from the nanoparticles and precipitate, leaving the nanoparticles unprotected. The unprotected nanoparticles can then aggregate into clusters of particles. Upon cooling, the surfactant redissolves into the solution, which then coats the aggregated particles and prevent them from dissociating into smaller ones.

This invention is directed to novel compositions that allow autoclaving of nanoparticles with reduced or no particle size growth. These compositions provide for a modification of the surfactant adsorbed onto nanoparticles such that the nanoparticles do not agglomerate during autoclaving. This invention is also directed to a method of making such compositions.

BRIEF SUMMARY OF THE INVENTION

This invention is directed to a composition comprised of nanoparticles having a surface modifier adsorbed on the surface thereof and an anionic or cationic surfactant as a cloud point modifier associated therewith, which cloud point modifier is present in an amount sufficient to increase the cloud point of the surface modifier.

This invention is further directed to a method of making nanoparticles having a surface modifier adsorbed on the surface and an anionic or cationic surfactant as a cloud point modifier associated therewith, said method comprising contacting said nanoparticles with the cloud point modifier for a time and under conditions sufficient to increase the cloud point of the surface modifier.

DETAILED DESCRIPTION OF THE INVENTION

This invention is directed to a composition comprised of nanoparticles having a surface modifier adsorbed on the surface thereof and an anionic or cationic surfactant as a cloud point modifier associated therewith, which cloud point modifier is present in an amount sufficient to increase the cloud point of the surface modifier. In a preferred embodiment, the cloud point of the surface modifier is increased above the temperature for autoclaving of the nanoparticles to prevent agglomeration.

The nanoparticles useful in the practice of this invention include a surface modifier. Surface modifiers useful herein physically adhere to the surface of the x-ray contrast agent but do not chemically react with the agent or itself. Individually adsorbed molecules of the surface modifier are essentially free of intermolecular crosslinkages. Suitable surface modifiers can be selected from known organic and inorganic pharmaceutical excipients such as various polymers, low-molecular weight oligomers, natural products and surfactants. Preferred surface modifiers include nonionic and anionic surfactants.

Representative examples of surface modifiers include gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens TM, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxy propylcellulose, hydroxypropylmethylcellulose phthlate, noncrystalline cellulose, magnesium aluminum silicate, triethanolamine, polyvinyl alcohol, and polyvinylpyrrolidone (PVP). Most of these surface modifiers are known pharmaceutical excipients and are described in detail in the *Handbook of Pharmaceutical Excipients*, published jointly by the American Pharmaceutical Association and The Pharmaceutical Society of Great Britain, the Pharmaceutical Press, 1986.

Particularly preferred surface modifiers include polyvinylpyrrolidone, tyloxapol, poloxamers such as Pluronic TM F68 and F108, which are block copolymers of ethylene oxide and propylene oxide, and poloxamines such as Tetronic TM 908 (also known as Poloxamine 908), which is a tetrafunctional block copolymer derived from sequential addition of propylene oxide and ethylene oxide to ethylenediamine, available from BASF, dextran, lecithin, dialkylesters of sodium sulfosuccinic acid, such as Aerosol OT TM, which is a dioctyl ester of sodium sulfosuccinic acid, available from American Cyanimid, Duponol TM P, which is a sodium lauryl sulfate, available from DuPont, Triton TM X-200, which is an alkyl aryl polyether sulfonate, available from Rohm and Haas, Tween 80, which is a polyoxyethylene sorbitan fatty acid ester, available from ICI Specialty Chemicals, and Carbowax TM 3350 and 934, which are polyethylene glycols available from Union Carbide. Surface modifiers which have been found to be particularly useful include Tetronic 908, the Tweens TM, Pluronic F-68 and polyvinylpyrrolidone. Other useful surface modifiers include:

decanoyl-N-methylglucamide;
n-decyl β-D-glucopyranoside;
n-decyl β-D-maltopyranoside;
n-dodecyl β-D-glucopyranoside;
n-dodecyl β-D-maltoside;
heptanoyl-N-methylglucamide;
n-heptyl-β-D-glucopyranoside;

n-heptyl β-D-thioglucoside;
n-hexyl β-D-glucopyranoside;
nonanoyl-N-methylglucamide;
n-noyl β-D-glucopyranoside;
octanoyl-N-methylglucamide;
n-octyl-β-D-glucopyranoside;
octyl β-D-thioglucopyranoside; and the like.

A surface modifier useful in the present invention is tyloxapol (a nonionic liquid polymer of the alkyl aryl polyether alcohol type; also known as superinone or triton).

This surface modifier is commercially available and/or can be prepared by techniques known in the art.

The nanoparticles useful in the practice of this invention can be prepared according to the methods disclosed in U.S. Pat. No. 5,145,684, whose disclosure is incorporated herein by reference. Briefly, nanoparticles are prepared by dispersing a poorly soluble therapeutic or diagnostic agent in a liquid dispersion medium and wet-grinding the agent in the presence of grinding media to reduce the particle size of the contrast agent to an effective average particle size of less than about 400 nm. The particles can be reduced in size in the presence of a surface modifier.

A general procedure for preparing the particles useful in the practice of this invention follows. The therapeutic or diagnostic agent selected is obtained commercially and/or prepared by techniques known in the art as described above, in a conventional coarse form. It is preferred, but not essential, that the particle size of the coarse therapeutic or diagnostic substance selected be less than about 100 μm as determined by sieve analysis. If the coarse particle size of that agent is greater than about 100 μm, then it is preferred that the coarse particles of the therapeutic or diagnostic agent be reduced in size to less than 100 μm using a conventional milling method such as airjet or fragmentation milling.

The coarse therapeutic or diagnostic agent selected can then be added to a liquid medium in which it is essentially insoluble to form a premix. The concentration of the therapeutic or diagnostic agent in the liquid medium can vary from about 0.1–60%, and preferably is from 5–30% (w/w). It is preferred, but not essential, that the surface modifier be present in the premix. The concentration of the surface modifier can vary from about 0.1 to 90%, and preferably is 1–75%, more preferably 10–60% and most preferably 10–30% by weight based on the total combined weight of the drug substance and surface modifier. The apparent viscosity of the premix suspension is preferably less than about 1000 centipoise.

The premix can be used directly by wet grinding to reduce the average particle size in the dispersion to less than 400 nm. It is preferred that the premix be used directly when a ball mill is used for attrition. Alternatively, the therapeutic or diagnostic agent and, optionally, the surface modifier, can be dispersed in the liquid medium using suitable agitation, e.g., a roller mill or a Cowles type mixer, until a homogeneous dispersion is observed in which there are no large agglomerates visible to the naked eye. It is preferred that the premix be subjected to such a premilling dispersion step when a recirculating media mill is used for attrition.

Wet grinding can take place in any suitable dispersion mill, including, for example, a ball mill, an attritor mill, a vibratory mill, and media mills such as a sand mill and a bead mill. A media mill is preferred due to the relatively shorter milling time required to provide the intended result, i.e., the desired reduction in particle size. For media milling, the apparent viscosity of the prμmix preferably is from about 100 to about 1000 centipoise. For ball milling, the apparent viscosity of the premix preferably is from about 1 up to about 100 centipoise. Such ranges tend to afford an optimal balance between efficient particle fragmentation and media erosion.

The grinding media for the particle size reduction step can be selected from rigid media preferably spherical or particulate in form having an average size less than about 3 mm and, more preferably, less than about 1 mm. Such media desirably can provide the particles of the invention with shorter processing times and impart less wear to the milling equipment. The selection of material for the grinding media is not believed to be critical. However, preferred media have a density greater than about 3 g/cm$^3$. Zirconium oxide, such as 95% ZrO stabilized with magnesia, zirconium silicate, and glass grinding media provide particles having levels of contamination which are believed to be acceptable for the preparation of therapeutic or diagnostic compositions. However, other media, such as stainless steel, titania, alumina, and 95% ZrO stabilized with yttrium, are believed to be useful.

The attrition time can vary widely and depends primarily upon the particular wet grinding mill selected. For ball mills, processing times of up to five days or longer may be required. On the other hand, processing times of less than 1 day (residence times of about one minute up to several hours) have provided the desired results using a high shear media mill.

The particles must be reduced in size at a temperature which does not significantly degrade the therapeutic or diagnostic agent. Processing temperatures of less than about 30°–40° C. are ordinarily preferred. If desired, the processing equipment can be cooled with conventional cooling equipment. The method is conveniently carried out under conditions of ambient temperature and at processing pressures which are safe and effective for the milling process. For example, ambient processing pressures are typical of ball mills, attritor mills and vibratory mills. Processing pressures up to about 20 psi (1.4 kg/cm$^2$) are typical of media milling.

The surface modifier, if not present in the premix, must be added to the dispersion after attrition in an amount as described for the premix. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

The relative amount of therapeutic or diagnostic agent and surface modifier can vary widely and the optimal amount of the surface modifier can depend, for example, upon the particular therapeutic or diagnostic agent and surface modifier selected, the critical micelle concentration of the surface modifier if it forms micelles, the hydrophilic lipophilic balance (HLB) of the stabilizer, the melting point of the stabilizer, its water solubility, the surface tension of water solutions of the stabilizer, etc. The surface modifier preferably is present in an amount of about 0.1–10 mg per square meter surface area of the therapeutic or diagnostic agent. The surface modifier can be present in an amount of 0.1–90%, preferably 1–75%, more preferably 10–60%, and most preferably 10–30% by weight based on the total weight of the dry particle.

Therapeutic and diagnostic agents useful in the composition of the present invention include those disclosed in U.S. Pat. No. 5,145,684 and EP-A 498,482, whose disclosures are incorporated herein by reference. A preferred diagnostic agent is the x-ray imaging agent WIN-8883 (ethyl 3,5-diacetoamido-2,4,6-triiodobenzoate).

As used herein, particle size refers to a number average particle size as measured by conventional particle size measuring techniques well known to those skilled in the art, such as sedimentation field flow fractionation, photon correlation spectroscopy, or disk centrifugation. By "an effective average particle size of less than about 400 nm" it is meant that at least 90% of the particles have a weight average particle size of less than about 400 nm when measured by the above-noted techniques. In preferred embodiments of the invention, the effective average particle size is less than about 300 nm, and more preferably less than about 250 nm. In some embodiments of the invention, an effective average particle size of less than about 200 nm has been achieved. With reference to the effective average particle size, it is preferred that at least 95% and, more preferably, at least 99% of the particles have a particle size less than the effective average, e.g., 400 nm. In particularly preferred embodiments, essentially all of the particles have a size less than 400 nm. In some embodiments, essentially all of the particles have a size less than 250 nm.

A method for the preparation of a nanoparticle composition according to this invention includes the steps of introducing a therapeutic or diagnostic agent, a liquid medium, grinding media, and optionally, a surface modifier into a grinding vessel; wet grinding to reduce the particle size of the therapeutic or diagnostic agent to less than about 400 nm; and separating the particles and optionally the liquid medium from the grinding vessel and grinding media, for example, by suction, filtration or evaporation. If the surface modifier is not present during wet grinding, it can be admixed with the particles thereafter. The liquid medium, most often water, can serve as the pharmaceutically acceptable carrier. The method preferably is carried out under aseptic conditions. Thereafter, the nanoparticle composition preferably is subjected to a sterilization process.

As noted elsewhere herein, sterile filtration will not provide adequate sterilization for nanoparticles. Therefore, other methods of sterilization are required. For example, steam or moist heat sterilization at temperatures of about 121° C. for a time period of about 15 minutes can be used. At altitudes near sea level, such conditions are attained by using steam at a pressure of 15 pounds per square inch (psi) in excess of atmospheric pressure.

Dry heat sterilization may also be performed, although the temperatures used for dry heat sterilization are typically 160° C. for time periods of 1 to 2 hours.

Sterilization takes place in the presence of ionic cloud point modifiers, such as an anionic surfactant e.g., sodium dodecyl sulfate (SDS), capronic acid, caprylic acid, dioctylsulfosuccinate (DOSS), and sodium oleate, or a cationic surfactant, such as dodecyltrimethylammonium bromide (DTAB) and tetradecyl trimethyl ammonium bromide, also known as cetrimide (TTAB), which minimize particle size growth during sterilization.

The cloud point is the temperature at which the surface modifier (surfactant) precipitates out of solution as described above. By the phrase "cloud point modifier" is meant a compound which influences the cloud point of surface modifiers. In particular, the cloud point modifiers useful in the present invention raise the cloud point of the surface modifiers found adsorbed onto nanoparticles. In this way, the surface modifiers do not dissociate from the surface of the nanoparticles at temperatures used in autoclaving. Therefore, nanoparticles thus modified do not agglomerate during the sterilization process, and thus retain their effective average particle sizes of less than about 400 nm after sterilization.

The ionic cloud point modifier can be present in an amount of 0.005-20%, preferably 0.01-15%, more preferably 0.05-10%, by weight based on the total weight of the nanoparticle suspension.

Isotonicity refers to the osmotic pressure of a solution. A solution which will be administered into the blood stream of an individual is typically prepared such that the osmotic pressure of that solution is the same as the osmotic pressure of blood. Such a solution is said to be isotonic.

An isotonicity maintaining compound is a compound which provides for the maintenance or alteration of a solution so as to make that solution isotonic. Such an isotonicity maintaining compound will adjust the osmotic pressure of a solution containing the compositions of the present invention so as to provide, or maintain, an isotonic solution.

Exemplary isotonicity maintaining compounds include mannitol, dextrose, sodium chloride, potassium chloride, Ringer's lactate, etc. Preferred isotonicity maintaining compounds include mannitol and dextrose.

The pH value of a solution is also an important factor. Typically, pH values should not be either too acidic or too basic. To maintain the pH value of a solution, it is preferrable to provide pH value maintaining compounds. These compounds provide a buffering capacity to the solution, to prevent extremes of pH values of the solution upon storage or upon subsequent manipulation.

Exemplary pH value maintaining compounds include the well known buffers such as Tris base, HEPES, carbonate, phosphate, acetate and citrate salts. A preferred buffer is sodium phosphate (either mono- or di-basic, or both).

This invention further discloses a method of making nanoparticles having a surface modifier adsorbed on the surface and an anionic or cationic cloud point modifier associated therewith, comprised of contacting said nanoparticles with the cloud point modifier for a time and under conditions sufficient to increase the cloud point of the surface modifier.

This method involves the preparation of therapeutic or diagnostic nanoparticles, as discussed elsewhere herein, and contacting those nanoparticles with an ionic cloud point modifier. Contacting may be by admixing a suspension of nanoparticles with a solution of cloud point modifier. In a preferred embodiment, the method is followed by sterilization at a temperature and for a time sufficient to effect sterilization of the nanoparticle suspension. A preferred method of sterilization is steam autoclaving.

The following examples further illustrate the invention and are not to be construed as limiting of the specification and claims in any way.

EXAMPLE 1: WIN-8883/Tyloxapol formulation

WIN-8883 nanoparticle suspensions are most likely negatively charged. Therefore, a positively charged surfactant should attach itself very well to the surface of the particle, as a result of ionic interactions. WIN-8883 disperses very well in Tyloxapol (3%) solution. However, Tyloxapol has a very low cloud point (98° C.). To raise the cloud point, various ionic (both cationic and anionic) cloud point modifiers were used.

Results of cloud point measurement are shown in Table 1. Neither polyethylene glycol (PEG-400) nor propylene glycol (PG) is effective in raising the cloud point of Tyloxapol. Anionic surfactants such as DOSS, SDS and sodium oleate are very effective in raising the cloud point of Tyloxapol. The cationic surfactants tested [dodecyl trimethyl ammonium bromide (DTAB) and tetradecyl trimethyl ammonium bromide (TTAB)] are also very effective in raising the cloud point of Tyloxapol. Salts such as TRIS and phosphate lower the cloud point of Tyloxapol, phosphate having a stronger effect than TRIS.

TABLE 1

Effect of Ionic and Nonionic Additives on the Cloud Point of Tyloxopol (1%)

| Additive | Concentration | Cloud Point (°C.) |
|---|---|---|
| Control (none) | | 94 |
| PEG-400 | 10% (w/v) | 105 |
| | 5% | 100 |
| | 2% | 96 |
| Propylene Glycol | 2% | 98 |
| SDS | 0.5% | >131 |
| | 0.2% | >131 |
| | 0.1% | >131 |
| | 0.05% | 127 |
| | 0.01% | 115 |
| DOSS | 0.2% | >131 |
| | 0.1% | >131 |
| | 0.05% | >131 |
| | 0.01% | 116 |
| Sodium oleate | 0.5% | >131 |
| | 0.2% | >131 |
| | 0.05% | 123 |
| | 0.01% | 116 |
| DTAB | 0.5% | >131 |
| | 0.2% | 131 |
| | 0.1% | 122 |
| | 0.05% | 114 |
| TTAB | 0.5% | >131 |
| | 0.2% | >131 |
| | 0.1% | >131 |
| | 0.05% | >131 |
| | 0.01% | 110 |
| Sodium phosphate, pH 6.5 | 4 mM | 93 |
| | 10 mM | 92 |
| TRIS Buffer, pH 7.5 | 10 mM | 93 |
| Diatrizoic Acid | 0.1% | 124 |
| | 0.33% | 128 |
| Taurodeoxycholate | 0.1% | 123 |
| | 0.2% | 129 |

EXAMPLE 2: Particle size of WIN-8883/Tyloxapol

Results indicate that when formulated with a small amount of ionic surfactant as a cloud point modifier, either anionic or cationic, WIN-8883/Tyloxapol nanoparticle suspensions remain unchanged in particle size after autoclaving at 121° C. for 20 minutes. The results are shown in Table 2.

The results are consistent with the effect of cloud point modifiers on the cloud point of Tyloxapol. Those that raised the cloud point (SDS, DOSS, DTAB, CTAB) showed strong stabilization effect whereas those with little or no effect on cloud point (PEG) showed no stabilization effect.

Also, it appears that low concentration of buffer, either phosphate or TRIS can be added without much detrimental effect.

TABLE 2

Stabilizing Effect of Ionic Surfactants on a Nanoparticle Suspension (15% WIN 8883/3% Tyloxapol), pH 4.2

| Additive | Autoclave Sterilization 121° C./20 min. | Mean Particle Size (nm) | Polydispersity |
|---|---|---|---|
| none | no | 158 | 0.102 |
| none | yes | 445 | 0.231 |
| 5% PEG-400 | yes | 453 | 0.246 |
| 10% PEG-400 | yes | 507 | 0.197 |
| 10% PEG + 0.5% DTAB | yes | 237 | 0.134 |
| 0.5% DTAB | yes | 209 | 0.182 |
| 0.3% DTAB | yes | 245 | 0.178 |
| 0.2% DTAB | yes | 250 | 0.179 |
| 0.3% TTAB | yes | 295 | 0.209 |
| 0.5% SDS | yes | 185 | 0.115 |
| 0.3% SDS | yes | 188 | 0.135 |
| 0.2% SDS | yes | 185 | 0.131 |
| 0.1% SDS | yes | 190 | 0.134 |
| 0.5% DOSS | yes | 176 | 0.158 |
| 0.3% DOSS | yes | 190 | 0.116 |
| 0.2% DOSS | yes | 188 | 0.136 |
| with 10 mM Sodium Phosphate buffer (pH 6.65) | | | |
| none | yes | 406 | 0.187 |
| 0.2% DTAB | yes | 350 | 0.117 |
| 0.2% DOSS | yes | 185 | 0.137 |
| 0.1% SDS | yes | 179 | 0.155 |

EXAMPLE 3: Cloud Point Analysis of Tyloxapol

In order to determine the effect of various buffers and various surfactants on the cloud point of Tyloxapol, the following general methodology was used. First, using 5 milliliter treated Wheaton vials, the amount of the additives to be tested were weighed into each vial. Next, 2.0 ml of a 1% Tyloxapol stock solution was added to each vial. The vials were then placed in a PEG-400 bath and the temperature was increased slowly to observe the solution turning cloudy. The results of these experiments are shown in Table 3.

TABLE 3

Cloud Point Determination of Tyloxapol (1%)

| Additive | Cloud Point (°C.) | Increase of C.P |
|---|---|---|
| None | 95 | 0 |
| 10% PEG-400 | 105 | 10 |
| 5% PEG-400 | 100 | 5 |
| 0.5% SDS | >131 | >36 |
| 2% Propylene Glycol | 98 | 3 |
| 0.2% DTAB | 131 | 36 |
| 0.5% DTAB | >131 | >36 |
| 0.5% TTAB | >131 | >36 |
| 0.5% Sodium Oleate | >131 | >36 |
| 0.5% DOSS | >131 | >36 |

EXAMPLE 4: Effect of SDS and DOSS on the particle size of EEDA nanoparticles

DOSS and SDS samples were prepared by adding specific volumes of DOSS or SDS stock solution (in 3% Tyloxapol) to nanoparticle solutions as in Example 3. Samples were autoclaved in the steam autoclave at 121° C. as indicated in the Table. The results are shown in Table 4.

TABLE 4

| Particle Size Analysis of WIN 8883/Tyloxapol Nanoparticle Suspension Sample: 15% WIN 8883, 3% Tyloxapol. Average particle size: 159 nm Autoclaved at 121° C. for 20 min. | | |
|---|---|---|
| Additive | Mean Particle Size (nm) | Poly dispersity |
| none | 445 | 0.231 |
| 0.05% SDS | 376 | 0.1 |
| 0.1% SDS | 186 | 0.129 |
| 0.04% DOSS | 415 | 0.183 |
| 0.1% DOSS | 189 | 0.125 |

EXAMPLE 5: Effect of Stabilizers and Isotonicity maintaining compound on the stability of WIN 8883 nanoparticles The addition of ionic cloud point modifiers and isotonicity maintaining compounds were tested in nanoparticle suspensions of WIN 8883/Tyloxapol, as described in Example 3. The results are shown in Table 5.

TABLE 5

| Stabilizing Effect of Ionic Surfactants on WIN 8883 nanoparticles upon Autoclave Sterilization (all samples autoclaved at 121° C. for 20 min.) | | |
|---|---|---|
| Additive | Mean Particle Size (nm) | Polydispersity |
| Sample: 15% WIN 8883, 3% Tyloxapol, pH 6.0 + 2.5% Glycerol | | |
| 0.2% DOSS | 181 | 0.22 |
| 0.2% DOSS | 184 | 0.17 |
| 0.2% SDS | 186 | 0.16 |
| Sample: 15% WIN 8883, 3% Tyloxapol, pH 6.0 + 5% Mannitol | | |
| 0.2% DOSS | 183 | 0.19 |
| 0.2% SDS | 186 | 0.13 |
| Sample: 15% WIN 8883, 3% Tyloxapol, pH 6.0 + 5% Dextrose | | |
| 0.2% DOSS | 182 | 0.17 |
| 0.2% SDS | 187 | 0.18 |

| Stabilizing Effect of Ionic Surfactants on Particle Size Distribution | | | |
|---|---|---|---|
| Additive | 121° C./ 20 min. | Z Ave. (nm) | Polydispersity |
| Sample: 15% WIN 8883, 0.93% Tyloxapol | | | |
| control (no additive) | no | 1577 | 0.362 |
| control (no additive) | yes | 1275 | 0.486 |
| 0.2% DOSS, 5% mannitol | yes | 471 | 0.31 |
| Sample: 15% WIN 8883, 2% Tyloxapol | | | |
| control (no additive) | no | 158 | 0.146 |
| control (no additive) | yes | 415 | 0.198 |
| 0.2% SDS, 5% mannitol | yes | 170 | 0.142 |
| 0.2% DOSS | yes | 170 | 0.157 |
| 0.2% SDS | yes | 168 | 0.083 |
| 0.2% SDS, 5% dextrose | yes | 170 | 0.098 |
| 0.2% DOSS, 5% mannitol | yes | 174 | 0.085 |
| 0.2% DOSS, 5% dextrose | yes | 169 | 0.139 |
| 0.1% SDS | yes | 180 | 0.139 |
| 0.1% DOSS, 5% mannitol | yes | 184 | 0.147 |
| 0.1% SDS, 5% mannitol | yes | 187 | 0.135 |
| 0.1% DOSS | yes | 183 | 0.087 |
| 0.1% SDS, 5% dextrose | yes | 180 | 0.159 |
| 0.1% DOSS, 5% dextrose | yes | 180 | 0.096 |
| Sample: 15% WIN 8883, 3% Tyloxapol | | | |
| control (no additive) | no | 143 | 0.06 |
| control (no additive) | yes | 452 | 0.167 |
| 0.2% DOSS, 5% dextrose | yes | 168 | 0.138 |
| 0.2% SDS, 5% mannitol | yes | 169 | 0.153 |
| 0.2% DOSS | yes | 168 | 0.108 |
| 0.2% SDS, 5% dextrose | yes | 169 | 0.12 |
| 0.2% SDS | yes | 163 | 0.159 |

TABLE 5-continued

| | | | |
|---|---|---|---|
| 0.2% DOSS, 5% mannitol | yes | 169 | 0.126 |

The foregoing specification, including the specific embodiments and examples is intended to be illustrative of the present invention and is not to be taken as limiting. Numerous other variations and modifications can be effected without departing from the true spirit and scope of the present invention.

We claim:

1. A compound comprised of nanoparticles consisting essentially of a crystalline diagnostic or therapeutic agent and a non-crosslinked nonionic surfactant adsorbed on the surface thereof and an anionic or cationic cloud point modifier associated therewith, which cloud point modifier is present in an amount of 0.005–20% by weight based on the total weight of the composition and sufficient to increase the cloud point of the surface modifier, wherein said nanoparticles are resistant to particle size growth when said composition is heat sterilized at 121° C. for 15 minutes.

2. The composition of claim 1 wherein said nanoparticles contain a diagnostic agent.

3. The composition of claim 1 wherein said surface modifier is tyloxapol.

4. The composition of claim 2 wherein said diagnostic agent is ethyl 3,5-diacetoamido-2,4,6-triiodobenzoate.

5. The composition of claim 1 wherein said anionic cloud point modifier is selected from the group cosisting of sodium dodecyl sulfate, dioctylsulfosuccinate, taurodeoxycholate and sodium oleate.

6. The composition of claim 1 wherein said cationic cloud point modifier is selected from the group consisting of dodecyltrimethylammonium bromide and tetradecyl trimethyl ammonium bromide.

7. The composition of claim 1 further comprising an isotonicity maintaining compound.

8. The composition of claim 7 wherein said maintaining compound is selected from the group consisting of mannitol or dextrose.

9. The composition of claim 1 further comprising a pH value maintaining compound.

10. The composition of claim 9 wherein said pH value maintaining compound is sodium phosphate.

11. The composition of claim 1 in wherein said cloud point modifier increases the cloud point of said surface modifier above the sterilization temperature of the nanoparticles.

12. A method for of making nanoparticles having a surface modifier adsorbed on the surface and an anionic or cationic cloud point modifier associated therewith, comprised of contacting said nanoparticles with the cloud point modifier for a time and under conditions sufficient to increase the cloud point of the surface modifier.

13. The method of claim 12 further comprising the step of sterilizing said nanoparticle.

14. The method of claim 13 wherein said sterilizing is by steam heat autoclaving.

15. The composition of claim 1 wherein said nonionic surfactant is selected from the group consisting of polyoxyethylene alkyl ethers, polyoxyethylene castor oil derivatives, polyoxyethylene sorbitan fatty acid esters, polyoxyethylene stearates, tyloxapol, poloxamers, and poloxamines.

* * * * *